(12) United States Patent
Sangouard et al.

(10) Patent No.: US 6,409,656 B1
(45) Date of Patent: Jun. 25, 2002

(54) ARTIFICIAL SPHINCTER WITH MAGNETIC CONTROL

(76) Inventors: Patrick Sangouard, 20, chemin des Boutareines - F -, 94350 Villiers sur Marne; Bernard Greillier, 38, avenue des Frères Lumière - F -, 69008 Lyons, both of (FR)

( * ) Notice: Subject to any disclaimer, the term of this patent is extended or adjusted under 35 U.S.C. 154(b) by 0 days.

(21) Appl. No.: 09/529,708
(22) PCT Filed: Oct. 13, 1998
(86) PCT No.: PCT/FR98/02184
§ 371 (c)(1),
(2), (4) Date: May 8, 2000
(87) PCT Pub. No.: WO99/18885
PCT Pub. Date: Apr. 22, 1999

(30) Foreign Application Priority Data

Oct. 15, 1997 (FR) ............................. 97 12918

(51) Int. Cl.⁷ ............................. A61F 2/02; F04B 17/00
(52) U.S. Cl. ............................. 600/30; 417/420
(58) Field of Search ............................. 600/29, 30, 31, 600/32, 16, 17; 623/3.11; 417/420; 604/129, 320; 251/65

(56) References Cited

U.S. PATENT DOCUMENTS

| 3,926,175 A | | 12/1975 | Allen et al. |
| 4,053,952 A | | 10/1977 | Goldstein |
| 4,351,322 A | * | 9/1982 | Prager ......................... 600/32 |
| 5,380,268 A | * | 1/1995 | Wheeler ....................... 600/30 |
| 5,562,598 A | | 10/1996 | Whalen et al. |
| 5,634,878 A | * | 6/1997 | Grundei et al. ............... 600/30 |
| 5,762,599 A | * | 6/1998 | Sohn ........................... 600/30 |

FOREIGN PATENT DOCUMENTS

| FR | 2651134 | 3/1991 |
| FR | 2655536 | 6/1991 |
| FR | 2688693 A | 9/1993 |

* cited by examiner

Primary Examiner—John P. Lacyk
Assistant Examiner—Nikita R Veniaminov
(74) Attorney, Agent, or Firm—Davis & Bujold, P.L.L.C.

(57) ABSTRACT

The present invention relates to an artificial sphincter provided with a valve implanted permanently on a duct or an organ, whether biological or not, during a surgical operation and which can then be easily activated from outside the human body by the patient and also easily adjusted from outside the human body during a postoperative session by a doctor. The valve (17) of the artificial sphincter comprises a rigid and airtight housing (1, 3, 16), provided with a support conduit (11) receiving the duct (2), and a strap (4) compressing this duct against a wall of the conduit, this strap being kept tight by a spring mechanism (12) which presses a lower disk (6) bearing a first magnet (9), the whole assembly being mobile in axial translation in the housing. It also comprises an upper disk (14) screwed in the housing, forming an axial stop for the first magnet and bearing a second magnet (15). A permanent magnet (18) outside the human body makes it possible to activate the first magnet (9) to loosen the strap (4) and open said duct (2). A rotating electromagnet (27) outside the human body makes it possible to make the second magnet (15) and the upper disk (14) rotate to adjust the tension of the strap and the degree of closure of the duct (2).

16 Claims, 5 Drawing Sheets

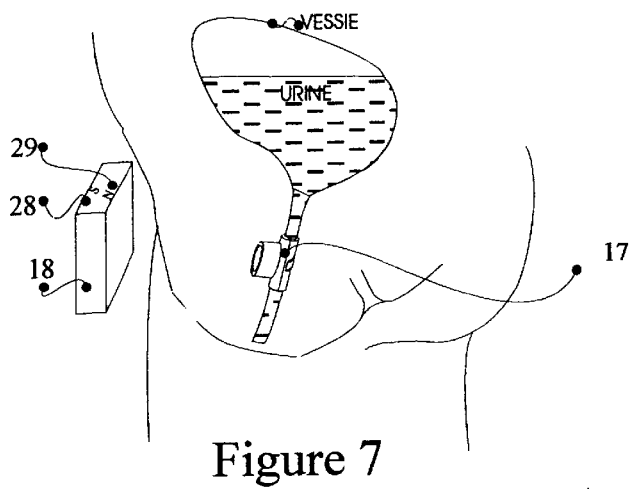
Figure 7
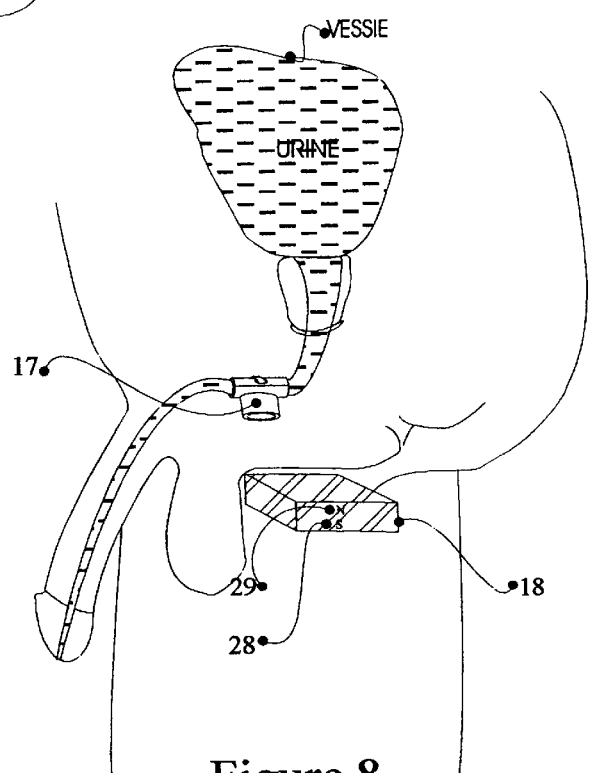
Figure 8
Figure 9

ARTIFICIAL SPHINCTER WITH MAGNETIC CONTROL

FIELD OF THE INVENTION

The present invention relates to an artificial sphincter with magnetic control comprising a valve designed to be installed permanently on a biological duct or organ in the human body and provided with means of mechanically closing said duct comprising a first element which is sensitive to a magnetic field and means of magnetic control outside said human body and designed to activate said first element sensitive to a magnetic field.

BACKGROUND OF THE INVENTION

There are known sphincter prostheses consisting of a toric balloon which tightly hugs the urethra, this balloon being able to be inflated by means of a small syringe made of flexible synthetic material and placed in a man's testicles or a woman's labia majora. An auxiliary reservoir, placed in the viscers and linked by tubes to the syringe and balloon, makes it possible to inflate or deflate the latter using a physiological fluid propulsed by the syringe. This reservoir houses a device making it possible to reverse the direction of flow of the fluid which inflates and deflates the balloon. The surgical installation of this urinary prosthesis is quite tricky as it is made up of three subassemblies linked to a pipe in which a physiological fluid flows. It can therefore present leakage risks, is relatively bulky and is insufficiently ergonomic which thereby contributes to the psychological discomfort of the patient. Furthermore, the size of the balloon can only be adjusted in notches and inflating it leads to folds which bring about excessive compression points on the urethra which may lead to a local necrosis of the tissues. Finally, the reservoir's reversing device may jam, preventing the unit from operating.

This type of sphincter prostheses has been improved by providing a device for controlling the physiological fluid which is controlled by magnetic means outside the human body as divulged for example in the publications U.S. Pat. No. 053,952 and U.S. Pat. No. 5,562,598. Nevertheless, these sphincter prostheses remain complex because of the various components required and the risks of the physiological fluid leaking persist.

Other publications like for example FR-A-2 655 536 and FR-A-2 651 134 describe sphincter prostheses requiring the presence of a balloon to hold the prosthesis and collect the urine in the bladder. They are therefore tricky to put in place and require a flexible tube with its closing and opening mechanism to be permanently present in the man's penis or the woman's urinary meatus. This system of course causes the user considerable discomfort, particularly during sexual intercourse.

Other artificial sphincters do exist which do not operate with a physiological fluid but by means of a mechanical valve controlled directly by a magnetic field applied outside the human body, as described for example in publications FR-A-2 688 693 and U.S. Pat. No. 3,926,175. In the first publication, the artificial sphincter is comprised of a mechanical clip provided around the duct to be sealed and one of its branches is coupled to a solenoid controlled by an internal energy sensor. This sensor receives waves from a transmitter outside the human body, converts them and transmits them to the solenoid to open the clip. In the second publication, the artificial sphincter is made up of a mechanical valve, part of which comprises a permanent magnet activated by an electromagnet arranged outside the human body. In both cases, the magnetic control only controls the valve of the artificial sphincter in on-off mode, i.e. only opening or closing it. None of these devices makes it possible to adjust the degree to which this mechanical valve is closed.

In another application, there is also a sphincter prosthesis comprising an adjustable ring placed by means of surgery around the stomach for patients suffering from obesity, with the aim of helping them to lose weight. This device, comprised of a ring made of biocompatible flexible material, called a balloon, is fitted with a closing loop at its ends and is connected by a fill-up tube to an airtight housing which is closed by a flexible membrane. The surgeon positions this ring around the stomach and connects it to the filling housing placed under the skin. During a physical examination, the practitioner can then adjust the tightness of the ring by puncturing in the housing through the patient's skin using a syringe and injecting or extracting a physiological fluid in the housing. This type of prostheses presents the drawback of being able to leak following injuries caused by the surgeon when putting it in place or following the formation of a hernia on the balloon's flexible pocket. It also presents the drawback of not being able to be finely and simply adjusted as it causes pain when puncturing under the skin to adjust the balloon.

The aim of the present invention is to overcome these difficulties and drawbacks by proposing an artificial sphincter comprising a valve which is implanted during a surgical operation and can then be activated easily from outside the human body by the patient and is also easily adjustable from outside the human body during a postoperative examination by a doctor. This artificial sphincter is designed to have several applications given the fact that it can be adjusted either to totally seal or to constrain a duct, like for example the urinary urethra, the colon, the pylorus of the stomach, or any other duct, but also any other organ whether biological or not. This artificial sphincter thus makes it possible, for example, to overcome the problems of bladder or bowel incontinence, to change in a controlled and remote manner the opening of the pylorus in a human being or the contraction of an organ, be it biological or not.

This aim is achieved by an artificial sphincter as described in the preamble and characterized in that it comprises means of adjusting the degree of closure of said means of closing the duct comprising a second element sensitive to a magnetic field designed to be controlled by a magnetic field generated by second means of magnetic control outside said human body.

SUMMARY OF THE INVENTION

In a preferred form of embodiment, the valve comprises an airtight housing placed on said duct and provided with a support conduit arranged to receive said duct in the open position, the means of closing the duct and the means of adjusting the degree of closure being mounted inside said housing.

The means of closure advantageously comprise at least one strap arranged to compress said duct against a wall of said support conduit, one at least of its ends being fixed to the first element sensitive to a magnetic field, mobile in axial translation in said housing.

Preferably, the means of closure comprise a spring mechanism which is mobile in axial translation in said housing, arranged between said support conduit and said first element and arranged to exert pressure on this magnet so as to move it away from said support conduit to tighten the strap.

The means of closure can furthermore comprise a lower disk which is mobile in axial translation in said housing, arranged between the spring mechanism and the first element and fixed to the other end of the strap.

In the preferred form of embodiment, the means of adjusting the degree of closure of said means of closing the duct comprise an upper disk mounted by screwing it in said housing and comprising a second element sensitive to a magnetic field, this upper disk forming an axial stop for said means of closure.

A thrust ball bearing can be advantageously arranged between the means of closure and the means of adjustment so as to eliminate any friction to facilitate the rotation of said upper disk.

The first means of magnetic control can comprise an external magnet having its poles arranged axially, designed to be arranged substantially opposite said valve and arranged to move said first element axially in the direction of the support conduit to loosen the strap.

The second means of magnetic control can also comprise an external rotating magnet having its poles arranged in a plane perpendicular to its axis, designed to be arranged substantially opposite said valve and arranged to make said second element rotate.

This magnet can comprise a U-shaped metal structure coupled to a motor, this structure bearing a coil supplied with an electric current, the speed of the motor and/or intensity of the current being variable.

Likewise, this magnet can comprise metal lugs mounted at the ends of said structure, the spacing between these lugs being adjustable to adjust the radial position of the poles.

The first element and/or the second element sensitive to a magnetic field is advantageously made up of a magnet but can also be made up of a metal part in some alternatives.

In a quite advantageous manner, the airtight housing is filled with a physiological fluid which is used as a shock absorber for the moving organs and is made of rigid, biocompatible plastic materials, the ends of the support conduit being flexible to ensure tightness with said duct.

BRIEF DESCRIPTION OF THE DRAWINGS

The present invention and its advantages shall be more fully disclosed in the following description of a form of embodiment provided by way of an unrestricted example and with reference to the attached drawings, in which:

FIG. 7 is an overall view of the implantation of the sphincter in a woman,

FIG. 8 is an overall view of the implantation of the sphincter for men, the FIG. 9 is an overall view of the valve.

DETAILED DESCRIPTION OF THE INVENTION

Figure 1:
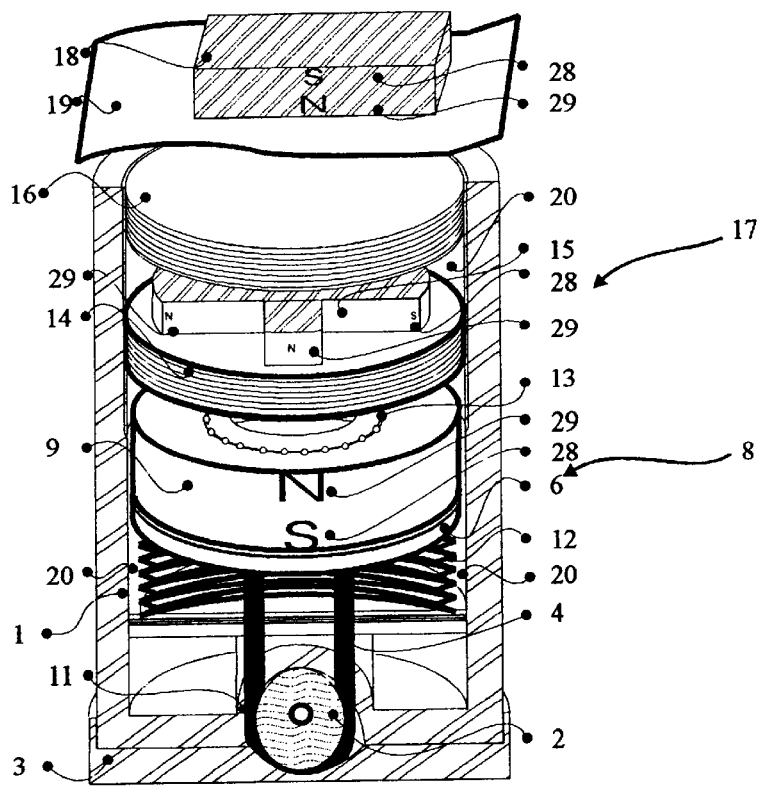
FIG. 1 is a perspective of the artificial sphincter valve in the open position, partially cutaway according to a plane passing the section of the duct to be sealed.
Figure 2:
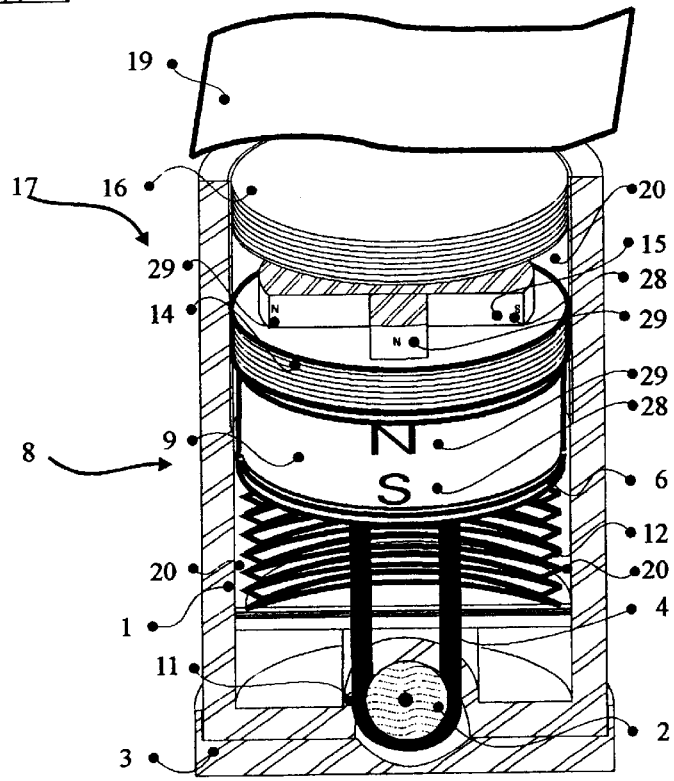
FIG. 2 is a similar view to FIG. 1, the valve being in the closed position.
Figure 3:
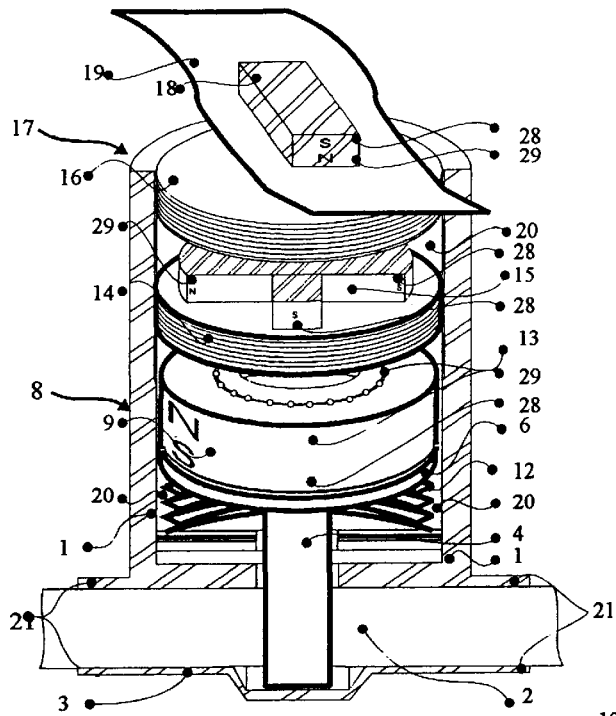
FIG. 3 is a perspective of the valve in the open position, partially cutaway according to a plane passing the axis of the duct to be scaled.
Figure 4:
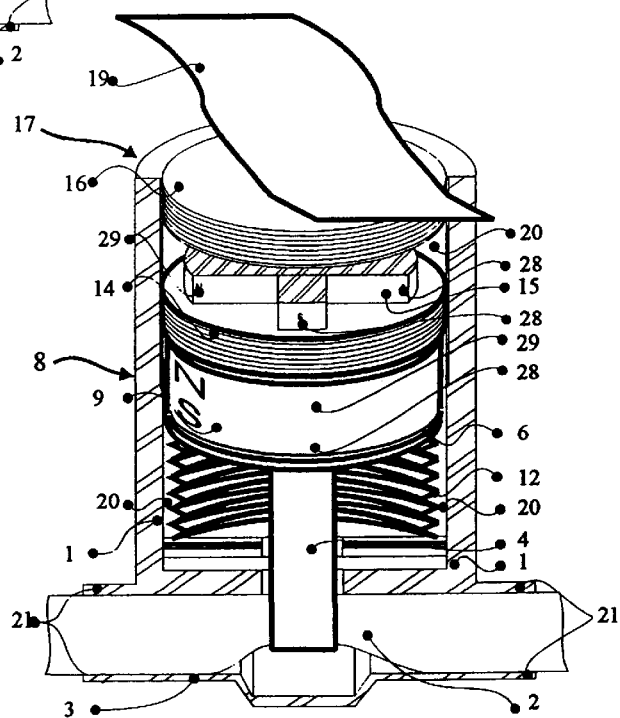
FIG. 4 is a similar view to FIG. 3, the valve being in the closed position.
Figure 5:
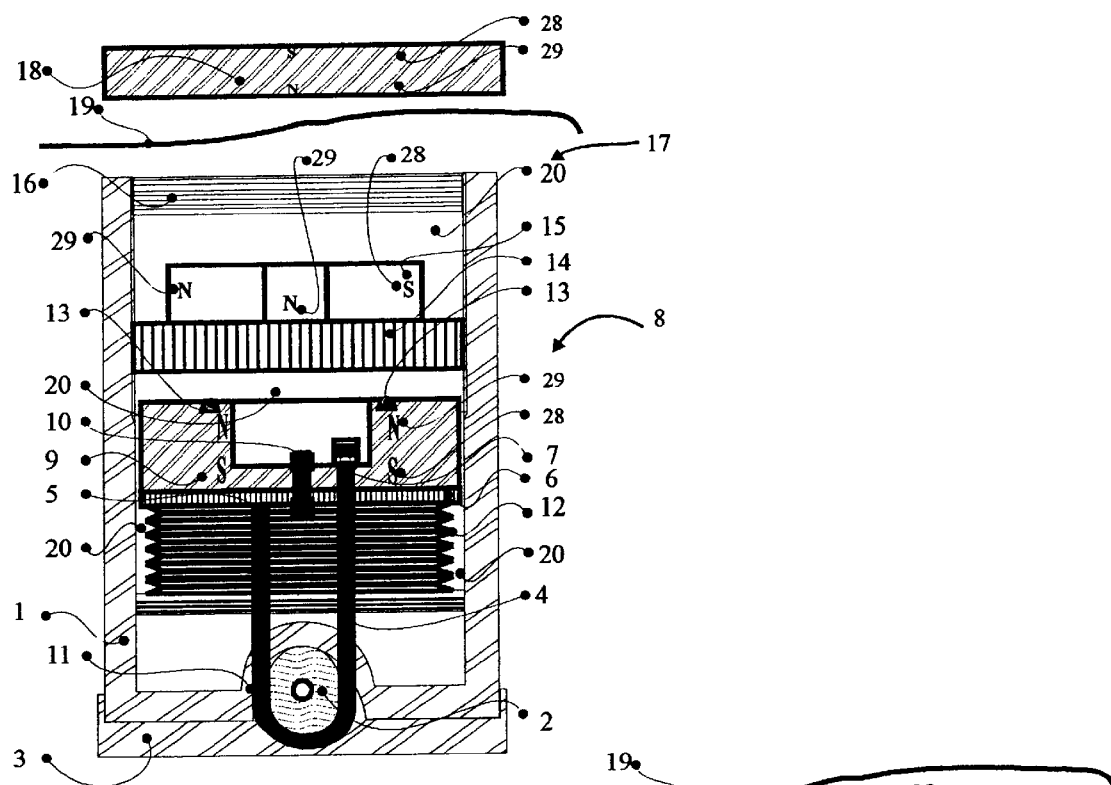
FIG. 5 is a cutaway view of the valve in FIG. 1.
Figure 6:
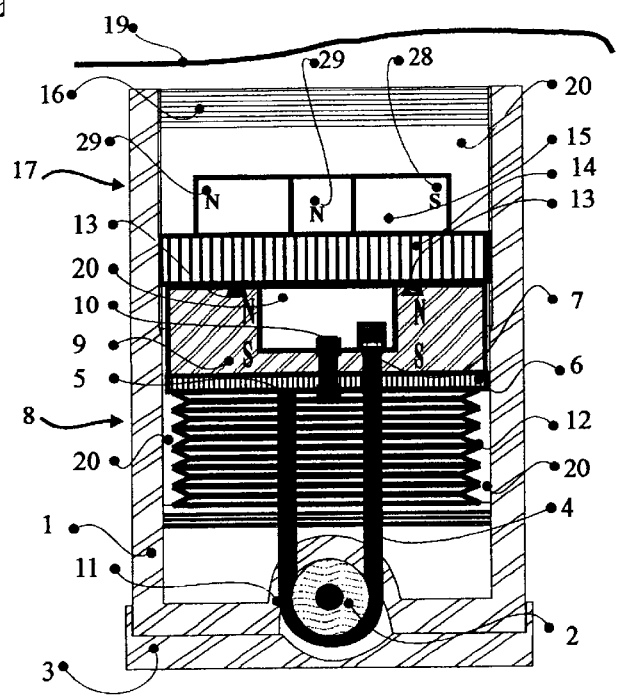
FIG. 6 is a cutaway view of the valve in FIG. 2.

With reference to FIGS. 7 and 8, the artificial sphincter according to the invention comprises a valve 17 designed to be installed permanently in the human body on a duct 2 or an organ whether biological or not, the opening and closing of which must be controlled mechanically. FIGS. 7 and 8 illustrate an example of the application of the artificial sphincter on the urethra respectively for women and men. The valve 17 is controlled remotely, by the patient, to switch from the closed position to the open position by a magnetic field created by means of a magnet 18 placed outside the epidermis 19 of said human body or any other suitable element capable of creating a magnetic field.

The valve 17 of the artificial sphincter according to the invention is now described in detail with reference to FIGS. 1 to 6 and 9. It comprises a T-shaped housing 1 designed to be placed on a duct 2 or an organ whether biological or not. This housing 1 is open and hollow, made out of rigid, biocompatible plastic materials, its horizontal branch being placed on the duct 2 parallel to its axis. It is sealed by an additional shell 3 placed on the other side of the duct 2 and assembled to said housing 1 by interlocking and clipping it on. As regards the duct 2, the housing 1 and the shell 3 define between them a support conduit 11 the section of which is at least equal to that of said duct 2. The ends 21 of this support conduit 11 are flexible to properly correspond to the external shape of said duct 2 and thereby ensure proper tightness. The housing 1 also defines an enclosure 20 oriented perpendicular to the support conduit 11 and arranged to receive the various components of said valve 17. This enclosure 20 is sealed by a cover 16 in biocompatible plastic materials assembled by interlocking and clipping it on, also ensuring proper tightness. This enclosure 20 is also filled with a physiological fluid which acts as a shock absorber when the various components move. The unit formed by the housing 1, the shell 3 and the cover 16 delimit a totally airtight environment, which is not in contact with the human tissues which avoids any problems of temporal cell invasion.

This valve 17 comprises mechanical means 8 of closing said duct 2 provided in particular with a flexible, flat strap 4 made of biocompatible material, arranged in a U shape so as to clasp and more precisely compress the duct 2 or the biological organ against one of the rigid walls of the support conduit 11. This strap 4 has its free ends 5, 7 linked to a lower disk 6 stressed by a spring mechanism 12 which keeps it permanently tight. More precisely, one of the free ends 5 of the strap 4 crosses the spring mechanism made up, for example, of a hollow bellows 12 and is fixed to the lower circular disk 6 made of plastic materials. This lower disk 6 can be secured to said bellows 12. The other end 7 of the strap 4 also crosses the bellows 12 then the disk 6 and is fixed to a first element 9 sensitive to a magnetic field. This first element 9 is secured to the lower disk 6 by means of a pin 10 provided in its center. In the example of embodiment described, this first element 9 sensitive to a magnetic field is a magnet, which can be permanent or not. However, in an alternative embodiment, it can be replaced by a simple metal part for example in the shape of a disk. In another less sophisticated alternative embodiment, the lower disk 6 and the first element 9 can be also replaced by a basic metal disk, the pin 10 being removed.

This magnet 9 is designed to move in axial translation in said housing 1 under the effect of the magnetic field generated by the external permanent magnet 18 when the latter is facing it outside the epidermis 19, these magnets each comprising a magnetic north 29 and a magnetic south 28 in a known manner. In this example, the magnetic south 28 and magnetic north 29 are arranged directly in line with the housing 1. The various parts, i.e. the bellows 12, the disk 6 and the magnet 9 have a diameter which is slightly smaller than that of the enclosure 20 arranged in said housing 1 so that they are not in contact with the inner wall of this housing 1 and can move axially without any friction.

The magnet 9 is topped with an upper circular disk 14 made of biocompatible plastic materials provided with an external thread co-operating with a corresponding thread provided on the inner wall of the housing 1. A thrust ball bearing 13 is provided between the upper disk 14 and the magnet 9 and is embedded in an annular groove arranged, for example, in said magnet 9. This thrust ball bearing 13 allows the upper disk 14 to rotate in the housing 1 with the minimum amount of friction, by screwing in or out according to the axis of said housing 1.

The upper disk 14 therefore forms an axial stop for the magnet 9, the lower disk 6 and the strap 4 which are permanently pushed towards this upper disk 14 by the bellows 12.

The upper disk 14 comprises a second element 15 sensitive to a magnetic field, for example, cross-shaped to limit the total weight of the valve 17. This second element 15 is used to adjust the axial position of the upper disk 14 and therefore the tension of the strap 4 during a postoperative operation as described later on. In the example of embodiment described, this second element 15 sensitive to a magnetic field is a magnet, which can be permanent or not. In an alternative embodiment, it can however be replaced by a basic metal part, for example disk-shaped. In another less sophisticated alternative embodiment, the upper disk 14 and the second element 15 can also be replaced by a basic metal disk.

The way in which the artificial sphincter according to the invention is put in place and operated shall now be described. The valve 17 of the artificial sphincter is put in place in the human body during an operation. The housing 1 is positioned on the duct 2 or the biological organ in question. One of the ends of the strap 4 is detached for example from the disk 6 to place the strap around this duct 2 and then fixed again. The shell 3 is put in place and assembled to the housing 1. During this operation, the surgeon determines the length of the strap 4 and the optimum adjustment of the mechanical means of closure 8 when he feels that the duct 2, locked in the support conduit 11 and clasped by the strap 4, is in a satisfactory constriction position stopping the flow of fluid or other material. Based on the position of the upper disk 14 in said housing 1, it is therefore a question of determining the idle position of the valve, corresponding in this case to the constriction of the duct 2. When the surgeon has finished installing and adjusting, he places the cover 16 to make the whole valve 17 airtight.

After the operation, the duct 2 is held in a permanent constriction position by the strap 4 which, kept tight by the bellows 12, compresses it against the support conduit 11. This bellows 12 exerts a permanent thrust in the direction of the upper disk 14 forming a stop for the lower disk 6 and the magnet 9. The unit formed by the strap 4, the lower disk 6 and the magnet 9 bearing the thrust ball bearing 13 moves in one piece and without any friction inside said housing 1 under the action of the bellows 12 keeping the strap 4 continually tight.

The decompression of the duct 2 is achieved by loosening the strap 4 when the bellows 12 is compressed under the effect of a magnetic field coming from the permanent magnet 18 arranged outside the epidermis 19. This permanent magnet 18, carried and operated by the patient, repels or attracts the other magnet 9 enclosed in said valve 17 depending on which direction the valve 17 was surgically implanted.

When the patient wishes to urinate for example, all (s)he has to do is place the permanent magnet 18 outside the abdomen opposite the magnet 9. If the magnetic pole of the external magnet 18 is the same as that of the permanent magnet 9 then the latter is repelled by the external magnet 18 generating a compression of the bellows 12 which has the effect of loosening the strap 4 and automatically causing the decompression of the duct 2 and therefore a flow of the fluid contained in this duct.

If the magnetic pole of the external magnet 18 is reversed, the movement of the magnet 9 is then blocked by the upper disk 14 in contact with the thrust ball bearing 13.

As soon as the magnet 9 is no longer activated by the external magnet 18, the bellows 12 returns to its idle position and automatically compresses the duct 2 again. Returning the bellows 12 to the idle position can furthermore be facilitated by simply turning the external magnet 18 to reverse the poles 28, 29.

Figure 10:
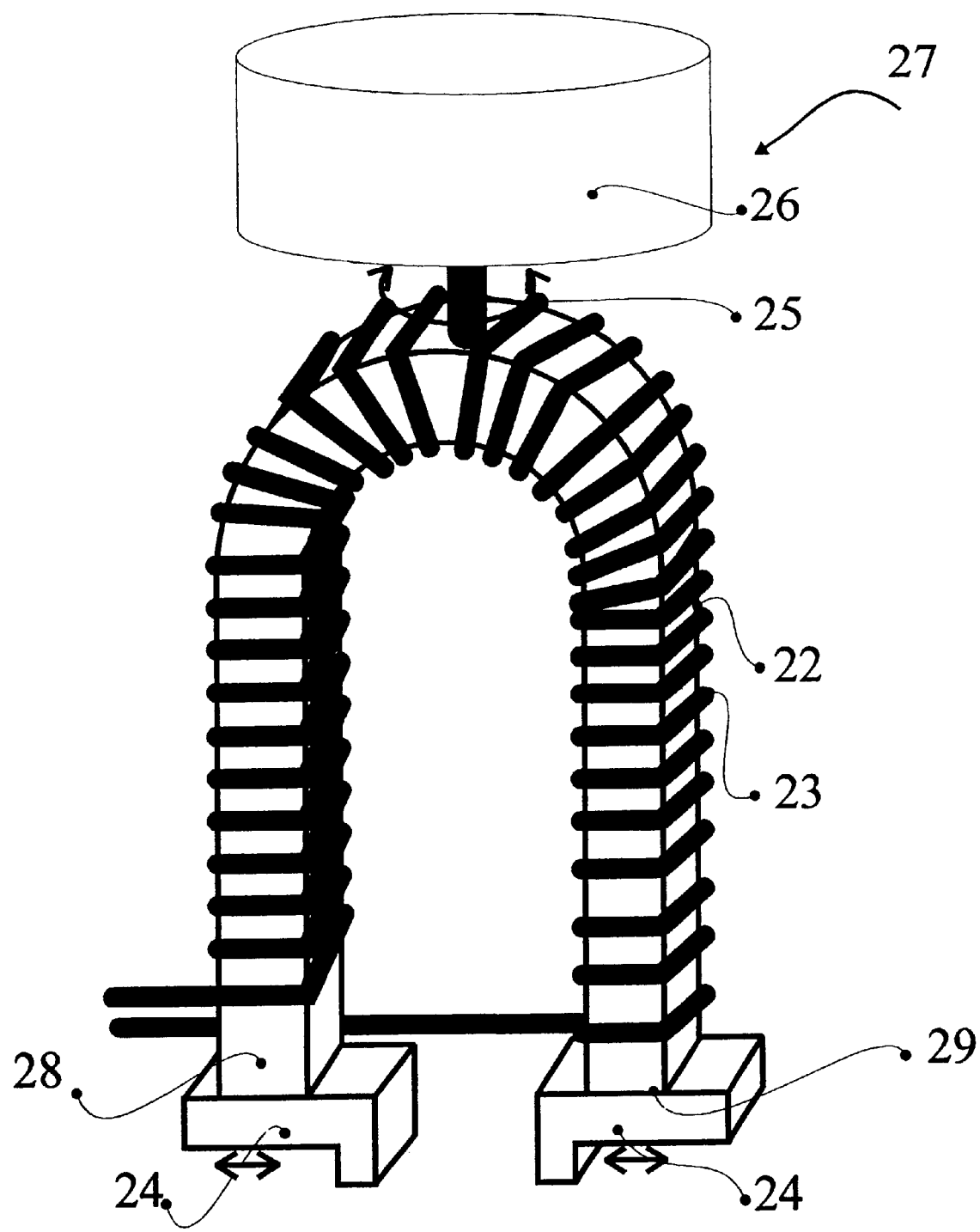
FIG. 10 is a perspective of the rotating electromagnet.

The artificial sphincter 17 according to the invention also comprises means of adjusting the degree of closure of said mechanical means 8 of closing the duct 2 without repeating a surgical operation, by means of an electromagnet 27 outside said human body represented by FIG. 10. This adjustment can be made necessary by the biological evolution through time of the duct 2 or the biological organ on which the valve 17 is mounted. This postoperative adjustment is possible by means of an external rotating magnetic field generated by the electromagnet 27 and applied to the magnet 15 to cause the upper disk 14 to rotate.

This adjustment is performed by a doctor equipped with said electromagnet 27. This electromagnet 17 creates a magnetic field providing current and a space between the magnetic south 28 and magnetic north 29 which is adjustable, and rotates at a speed which is also adjustable in a plane parallel to that of the magnet 15.

The electromagnet 27 represented by FIG. 10 comprises a metal structure 22 which is for example U-shaped and concentrates the magnetic field created by a coil 23 supplied with a direct electric current of adjustable intensity. Metal lugs 24 are mounted at the ends of the metal structure 22 so as to be able to adjust their spacing in order to adjust the spatial position of the magnetic north 29 and magnetic south 28 in relation to the corresponding poles of the magnet 15. The metal structure 22 is connected by means of a pin 25 to a variable speed electric motor 26. The whole electromagnet 27 can therefore rotate at an adjustable speed.

When the space between the magnetic norths 29 and magnetic souths 28 of the lugs 24 is correct and the electromagnet 27 is positioned opposite the magnet 15, then the rotation of the magnetic field created by the electromagnet 27 leads to the gyration of the magnet 15 moving the upper disk 14 guided by the thrust ball bearing 13. For this reason, the upper disk 14 secured to the magnet 15 is screwed or unscrewed in the housing 1 altering the axial position of the stop for the magnet 9 and the lower disk 6 and therefore altering the tension of the strap 4 and the degree of closure of the duct 2.

It therefore seems from this description that the invention makes it possible to achieve all the aims mentioned. Of course, the present invention is not restricted to the example of embodiment described and can be extended to include any modification and alternative which is obvious for the expert. This description relates to an artificial sphincter, the valve of which is mounted on a duct to be sealed like for example the urinary urethra but can be extended to any application in which it is necessary to control the closing and the opening of a duct but also in which it is necessary to control the contraction of a duct or an organ whether biological or not.

What is claimed is:

1. A magnetically controlled artificial sphincter valve (17) designed to be installed permanently on one of a duct (2) and an organ, whether biological or not, in a human body, the artificial sphincter valve (17) comprising;
   a mechanical means of closure (8) having a first element (9) sensitive to a first magnetic field for closing one of said duct and said organ within a desired degree of closure;
   an adjustment means (14) for adjusting a second element (15) sensitive to a second magnetic field to define the desired degree of closure;
   a first magnetic control means (18) located outside said human body designed to generate the first magnetic field to activate said first element; and
   a second magnetic control means (27) located outside said human body to generate the second magnetic field and adjust said second element (5) and regulate the degree of closure of said mechanical means (8) in closing one of said duct (2) and said organ.

2. The artificial sphincter valve (17) according to claim 1, further comprising an airtight housing (1, 3, 16) adapted to be placed on one of said duct (2) and said organ, and provided with a support conduit (11) arranged to receive one of said duct (2) and said organ in an open position and wherein the mechanical means (8) of closure and the adjustment means for regulating the degree of closure are mounted inside said housing.

3. The artificial sphincter valve (17) according to claim 2, wherein the mechanical means of closure (8) comprises at least one strap (4) having a first end (5) and a second end (7), arranged to compress one of said duct (2) and said organ against a wall of the support conduit (11), with at least one of said first and second ends of the strap being fixed to the first element (9) sensitive to a magnetic field and mobile in axial translation in said housing.

4. The artificial sphincter valve (17) according to claim 3, wherein the mechanical means of closure (8) comprises a spring mechanism (12) mobile in axial translation in said housing, arranged between said support conduit (11) and the first element (9) and arranged to exert pressure on the first element (9) so as to move the first element (9) away from the support conduit (11) to keep the strap (4) tight.

5. The artificial sphincter valve (17) according to claim 4, wherein the mechanical means of closure (8) comprises a lower disk (6) mobile in axial translation in the housing, arranged between the spring mechanism (12) and the first element (9) and fixed to one of said first and second ends (5, 7) of the strap (4).

6. The artificial sphincter valve (17) according to claim 3, wherein the first magnetic control means (18) comprises an external magnet having poles (28, 29) arranged axially, designed to be arranged substantially opposite said valve (17) and arranged to move said first element (9) axially in the direction of the support conduit (11) to loosen the strap (4).

7. The artificial sphincter valve (17) according to claim 2, wherein the adjustment means for adjusting the degree of closure of said mechanical means (8) of closing one of said duct and said organ comprises an upper disk (14) mounted in said housing (1), adjustable by rotational motion via the second element (15) sensitive to the second magnetic field, said upper disk (14) forming an axial stop for said mechanical means (8) of closing the duct.

8. The artificial sphincter valve (17) according to claim 7, wherein the second magnetic control means (27) comprises an external rotating magnet having poles (28, 29) arranged in a plane which is perpendicular to an axis of the external rotating magnet, designed to be arranged substantially opposite said valve (17) and arranged to make said second element (15) rotate.

9. The artificial sphincter valve (17) according to claim 8, wherein the external rotating magnet comprises a U-shaped metal structure (22) connected to a motor (26), said U-shaped metal structure (22) bearing a coil (23) supplied with an electric current, and wherein at least one of the speed of the motor (26) and the intensity of the current being variable.

10. The artificial sphincter valve (17) according to claim 9, wherein the magnet (27) comprises metal lugs (24) mounted at the ends of said U-shaped metal structure (22), and a spacing between the metal lugs (24) being adjustable to adjust the radial position of the poles (28, 29).

11. The artificial sphincter valve (17) according to claim 7, wherein a thrust ball bearing (13) is arranged between the mechanical means (8) of closing one of said duct and said organ and the adjustment means (14) for adjusting the degree of closure.

12. The artificial sphincter valve (17) according to claim 2, wherein at least the airtight housing (1, 3, 16) is made of rigid, bio-compatible plastic materials.

13. The artificial sphincter valve (17) according to claim 12, wherein the support conduit (11) is provided with ends (21) which are flexible to ensure a tight fit with one of said duct (2) and said organ.

14. The artificial sphincter valve (17) according to claim 2, wherein the airtight housing (1, 3, 16) is filled with a fluid used as a shock absorber for moving parts of the artificial sphincter valve (17).

15. The artificial sphincter valve (17) according to claim 1, wherein at least one of the first element (9) and the second element (15) sensitive to one of the respective first and second the magnetic fields comprises a magnet.

16. The artificial sphincter valve (17) according to claim 1, wherein at least one of the first element (9) and the second element (15) sensitive to one of the respective first and second the magnetic fields comprises a metal part.

* * * * *